United States Patent [19]
El-Rashidy et al.

[11] Patent Number: 5,888,534
[45] Date of Patent: *Mar. 30, 1999

[54] CONTROLLED RELEASE OF DRUGS DELIVERED BY SUBLINGUAL OR BUCCAL ADMINISTRATION

[75] Inventors: Ragab El-Rashidy, Deerfield; Bruce Ronsen, River Forest, both of Ill.; Emad Eldin Hassan, Alexandria, Egypt

[73] Assignee: Pentech Pharmaceuticals, Inc., Ill.

[ * ] Notice: The term of this patent shall not extend beyond the expiration date of Pat. No. 5,624,677.

[21] Appl. No.: 841,250

[22] Filed: Apr. 29, 1997

Related U.S. Application Data

[63] Continuation-in-part of Ser. No. 489,966, Jun. 13, 1995, Pat. No. 5,624,677.

[51] Int. Cl.$^6$ .................. A61K 9/22; A61K 9/26
[52] U.S. Cl. ............ 424/435; 424/464; 424/465; 424/468; 424/473; 514/770; 514/772.1; 514/772.2; 514/772.3; 514/774; 514/777; 514/778; 514/779; 514/781; 514/782
[58] Field of Search .................. 424/435, 473, 424/464, 468, 465

[56] References Cited

U.S. PATENT DOCUMENTS

| | | | |
|---|---|---|---|
| 2,818,855 | 1/1958 | Miller | 128/79 |
| 3,428,728 | 2/1969 | Lowey | 424/14 |
| 4,127,118 | 11/1978 | Latorre | 128/79 |
| 4,801,587 | 1/1989 | Voss et al. | 514/248 |
| 5,256,652 | 10/1993 | El-Rashidy | 514/58 |
| 5,419,917 | 5/1995 | Chen et al. | 429/469 |
| 5,624,677 | 4/1997 | El-Rashidy et al. | 424/435 |

OTHER PUBLICATIONS

Danjou, P. et al., *Br. J. clin. Pharmac.* 26: 733–739 (1988).

Deffond, D, et al. *J. Neurol. Neurosurg. and Psych.* 56: 101–103 (1993).

Droller, M.J. et al. Impotence. Consensus Development Conference Statement, National Institutes of Health *J.A.M.A.* 270:83–90 (1993).

Lal, S., et al. *Prog. Neuro–Psychopharmacol. & Biol. Psychiat.* 13:329–339 (1989).

Kirby, R.S., *British Medical J.* 308: 957–961 (1994).

Lal, S., et al. *Prog. Neuro–Psychopahrmacol. & Biol. Psychiat.* 13:329–339 (1989).

Muhtadi, F.J. and M.S. Hifnawy, "Analytical Profile of Apomorphine Hydrochloride," in *Analytical Profiles of Drug Substances*, Klaus Florely Ed., vol 20, Academic Press, Inc. New York (1991).

Murray, F.T. et al. *Amer. J. Medical Sci.* 309: 99–109 (1995).

O'Keefe, M., et al. *Medical Clinics of North America* 79: 415–434 (1995).

Segraves, R.T., "Dopamine agonists and their effect on the human penile erectile response," pp. 225–229 in Bancroft, J., ed. *The Pharmacology of Sexual Function and Dysfunction*, Excerpta Medica (Elsevier Science), Amsterdam, (1995).

Segraves, R,T, et al. *J. Urology* 145: 1174–1175 (1991).

Vickers, M.A. et al. *J. Urology* 149: 1258–1261 (1993).

*Primary Examiner*—Thurman K. Page
*Assistant Examiner*—James M. Spear
*Attorney, Agent, or Firm*—Olson & Hierl, Ltd.

[57] ABSTRACT

A composition providing a relatively slow release of water-soluble drugs, such as apomorphine, for delivery via the sublingual or buccal routes.

22 Claims, 6 Drawing Sheets

CONTROLLED RELEASE OF DRUGS DELIVERED BY SUBLINGUAL OR BUCCAL ADMINISTRATION

This is a Continuation-In-Part Application of copending U.S. Ser. No. 08/489,966, filed Jun. 13, 1995, which issued as U.S. Pat. No. 5,624,677.

FIELD OF THE INVENTION

This invention relates to a composition for the controlled release of water-soluble drugs for administration via either sublingual or buccal route. This invention also relates to a convenient treatment for psychogenic impotence and Parkinson's disease.

Reference to Related Application

Background of the Invention

The term "impotence" has been used to signify the inability of the male to attain and maintain erection of the penis sufficient to permit satisfactory sexual intercourse. The term "erectile dysfunction" has been suggested as a more precise term "to signify an inability of the male to achieve an erect penis as part of the overall multifaceted process of male sexual function." Droller, M. J. et al. *Impotence*. Consensus Development Conference Statement, National Institutes of Health (1993).

Erectile disfunction may result from psychological causes (psychogenic erectile dysfunction) or organic causes or a combination. organic causes include physiological, nervous, vascular and hormonal pathologies or a combination thereof.

The normal physiology of an erection involves nerve impulses which signal certain muscles to relax. These muscles, when contracted, restrict blood flow through arteries in the penis. When relaxed, the muscles permit a significant increase in blood flow. The increased blood flow engorges three groups of erectile tissue within the penis with blood and the penis becomes less flaccid. The engorged erectile tissue and the muscle structure of the penis depress adjacent veins, restricting the flow of blood out of the penis. The restriction of blood flow out of the penis increases and sustains the erection.

Deficiencies of some hormones, such as testosterone, or elevation of others, such as prolactin, can cause erectile dysfunction. Many drugs, such diuretics, antihypertensives, anticonvulsants, narcotics, alcohol, and psychotropic drugs may cause erectile disfunction as a side effect. Murray, F. T. et al. *Amer. J. Medical Sci.* 309: 99–109 (1995).

Damage to nerves and blood vessels may also provide an organic cause for erectile dysfunction. Disease processes may involve several aspects. For example, diabetes, which causes damage to both nerves and blood vessels, can cause erectile dysfunction. A significant percent of all diabetic men will suffer from erectile dysfunction.

Methods proposed for the treatment of erectile dysfunction have included external devices, sex therapy, surgical implantation of internal prostheses, injection of drugs directly into the penis and topically applied medications. None of these approaches is entirely effective.

External devices include tourniquets (see U.S. Pat. No. 2,818,855) and externally applied vacuum erection aids. While some clinicians consider externally applied erection aids as a first option for treatment, some patients are unwilling to use such devices. O'Keefe, M., et al. *Medical Clinics of North America* 79: 415–434 (1995).

Symptomatic sex therapy was originally found to be effective by Masters and Johnson, but later studies have not shown as impressive results. Freudian therapy does not appear to patients to be an attractive alternative. Vickers, M. A., et al. *J. Urology* 149: 1258–1261 (1993).

Surgically implanted mechanical devices, such as hinged or solid rods and inflatable, spring driven or hydraulic prostheses have been used for some time.

The administration of erection effecting and enhancing drugs is taught in U.S. Pat. No. 4,127,118 to LaTorre. This patent teaches a method of treating male impotence by injecting into the penis an appropriate vasodilator, in particular, an adrenergic blocking agent or a smooth muscle relaxant to effect and enhance an erection.

More recently, U.S. Pat. No. 4,801587 to Voss et al. teaches the application of an ointment to relieve impotence. The ointment consists of the vasodilators papaverine, hydralazine, sodium nitroprusside, phenoxybenzamine, or phentolamine and a carrier to assist absorption of the primary agent through the skin. U.S. Pat. No. 5,256,652 to El-Rashidy teaches the use of an aqueous topical composition of a vasodilator such as papaverine together with hydroxypropyl-β-cyclodextrin.

Recently the effect of apomorphine on penile tumescence in male patients afflicted with psychogenic impotence has been studied. Segraves, R, T, et. al. *J. Urology* 145: 1174–1175 (1991). These studies show that while apomorphine can indeed induce an erection in a psychogenic male patient, the apomorphine dose required to achieve a significant erectile response is usually accompanied by nausea or other serious undesirable side effects such as hypertension, flushing and diaphoresis.

Studies measuring the bioavailability, the bioavailable dose, the rate of absorption, elimination, and metabolism for apomorphine have been reported. Muhtadi, F. J. and M. S. Hitnawy, Analytical Profile of Apomorphine Hydrochloride, in *Analytical Profiles of Drug Substances*, Klaus Florely Ed., Vol 20, Academic Press, Inc. New York (1991). Traditional routes of administration, such as oral tablet and liquid preparations have been shown to be relatively ineffective in establishing a blood plasma level for this drug compared to parenteral administration. However, the sublingual route of administration has been investigated for the treatment of Parkinson's disease. In that study, sublingual apomorphine was found to be about 10% bioavailable compared to parenteral administration. Deffond, D, et al. *J. Neurol. Neurosurg. and Psych.* 56:101–103 (1993).

Sublingual tablets are well documented in the literature since the beginning of this century. The main reason for sublingual route of drug administration is to provide a rapid onset of action of potent drugs. Another reason is to avoid the first pass metabolism by the liver. The term "controlled release" when applied to sublingual tablets is limited to a maximum of about 60 minutes. Traditional sublingual tablets are usually designed as water soluble tablets made of water soluble sugars such as sorbitol, lactose, mannitol, etc. In the literature, controlled release sublingual tablets are very scarce.

Time release sublingual medications are disclosed in U.S. Pat. No. 3,428,728 issued to Lowey. (1969), perhaps due to the limited residence time in the sublingual cavity, or poor patient compliance, or acceptance of having a foreign body under the tongue for extended periods of time.

Lowey described a controlled release sublingual tablet made by cooking gum acacia and sorbitol (by heating) till partial dryness followed by addition of citric acid, color and flavor followed by cooling. Active ingredients such as nitroglycerin, caffeine, guaiocolate, amylase or isoproterenol were then added to the pourable paste that was cast into tablets. However, Lowey's discovery cannot be applied to make tablets by compression.

The time of release for a pharmaceutical preparation is critical to the effectiveness of the drug. An immediate release of the drug such as a solution of apomorphine placed under the tongue results in an overwhelming percentage of undesirable side effects. Heaton, J. P. W. et al. Recovery of erectile function by the oral administration of apomorphine *Urology* 45: 200–206 (1995). The sublingual tablet of the present invention provides a relatively slow controlled drug release as compared with a conventional soluble tablet, and thus dramatically reduces the undesirable side effects of drugs such as apomorphine.

What is needed is an effective treatment of psychogenic erectile dysfunction that involves minimal mechanical distractions and unwanted side effects.

SUMMARY OF THE INVENTION

The present invention provides compositions that release water-soluble drugs relatively slowly over an extended time period. The composition is suitable for dosage forms that deliver drugs by the sublingual or buccal routes. In the practice of this invention with its application to the pharmacological agent, apomorphine, a sublingual tablet formulation that includes particular constituents permits the drug to achieve its effective therapeutic plasma concentration which is below a plasma concentration where undesirable side effects such as nausea and vomiting occur. In addition to this major improvement arising from the present invention, the added benefit of drug release over a longer period of time from the tablet can increase the duration of the therapeutic activity for the drug.

The composition, in the form of a tablet, delivers the pharmacological agent, such as apomorphine, at a controlled rate to produce the desired physiological effect of the drug while preventing or diminishing the side effects such as hypotension, nausea and vomiting that have been associated with apomorphine. Such a composition thus provides the therapeutic benefits of apomorphine, as for example, in the treatment of Male Erectile Dysfunction and the management of motor fluctuations in Parkinson's disease with minimal side effects.

Delivery of a drug and producing a plasma concentration profile suitable for adequate therapeutic effect is a major goal of pharmaceutical sciences. Many drug substances are not well absorbed, or are inherently too unstable, or tend to produce significant undesired effects when administered by conventional oral route. A substance, such as apomorphine, is rapidly metabolized through this route. Yet, this drug has proven therapeutic benefit when administrated by parenteral route. Therefore, other routes of administration have been explored to gain the medicinal benefit for drugs such as apomorphine.

The previously available controlled release sublingual tablet formulation had a number of deficiencies. The present invention addresses these deficiencies, especially in the following areas.

1. Time of release. The time of release was limited from 15 to 60 minutes for a sublingual controlled release tablets in previous studies. Defond, et al. However, such time frame may not be practical in the case of certain diseases and illnesses. Similarly, this time window may be unacceptable for a number of pharmacological agents.

2. Mechanism of controlling the release of the pharmacological agent. For water soluble drugs, such as apomorphine, a hydrophilic diffusion- controlling matrix containing a water dispersible polymer will serve to retard dissolution and release of the pharmacological agent to within a time frame suitable for sublingual delivery. The presence of an osmotic agent, e.g., mannitol, along with hydrophilic, swellable, carrier there will also prevent severe retardation of drug release time.

3. Stabilization of the pharmacological agent. Because of the lability associated with many pharmacological agents, such as apomorphine, the imbedding of the pharmacological agent into a polymer matrix can reduce the contact of the agent with ambient oxygen, moisture and light. Thus the selection of materials should yield an enhanced stability for the pharmacological agent.

Drugs that are substantially water soluble, when released by a sublingual tablet, will rapidly dissolve into the surrounding fluid, be absorbed through the oral mucosa and be subsequently removed from the site of absorption. Absorption is related to the solubility of the drug substance. If the drug is a mineral acid salt, the absorption by the mucosal membrane may be slowed. The present invention is useful in determining the colligative properties of a pharmaceutical preparation for a water soluble drug substance designed for mucosal absorption.

The present composition consists essentially of a water-soluble drug, an osmotic agent, a swellable hydrophilic carrier and a water dispersible polymer. Suitable ingredients are described below and listed in Table 1, below. Water-soluble drugs that are suitable include apomorphine HCl, albuterol sulfate, timolol maleate, verapamil HCl, and naloxone HCl.

The suitable osmotic agents include monosaccharide and disaccharide sugars, such as glucose, fructose, mannitol, sorbitol, lactose, and sucrose. Glycerin or urea may also be used. Organic and inorganic salts, such as sodium chloride, potassium chloride and water soluble polyelectrolytes, are also suitable as osmotic agents. A preferred osmotic agent is mannitol.

The hydrophilic carrier may be chosen from fillers suitable for use in compositions made by the wet granulation process. Suitable hydrophilic carriers are microcrystalline cellulose, ethyl cellulose, cross-linked polyvinylpyrrolidone, fumed silica, silica, dicalcium phosphate, and calcium carbonate. Microcrystalline cellulose is a preferred hydrophilic carrier.

The swellable hydrophilic carrier comprises from about 25 weight percent to about 40 weight percent of the composition based on the weight of the composition.

The water dispersible polymer may be a gum, alginate, cellulose derivatives, gelatin, water soluble starch or other polymer. Suitable gums include gum tragacanth, gum acacia and guar gum; gum tragacanth is preferred. Suitable cellulose derivatives include methylcellulose, carboxymethylcellulose, hydroxymethylcellulose, hydroxypropyl methylcellulose A preferred cellulose derivative is hydroxypropyl methylcellulose (Methocel E4M Premium, NF).

The water dispersible polymer comprises from about 0.5 weight percent to about 20 weight percent of the composition based on the weight of the composition. Preferably the water dispersible polymer comprises from about 6 weight percent to about 10 weight percent of the composition based on the weight of the composition.

The ratio of the amount by weight of the osmotic agent to the amount by weight of the swellable hydrophilic carrier is in the range of about 0.3 to about 4. Preferably for the dosage forms containing a relatively higher amount of the active ingredient, i.e., in the range of about 10 to about 40 milligrams, the ratio of the amount by weight of the osmotic agent to the amount by weight of the swellable hydrophilic carrier is in the range of about 0.35 to about 2. For the dosage forms containing a relatively lower amount of the active ingredient, i.e., in the range of about 2 to about 10 milligrams, the ratio of the amount by weight of the osmotic agent to the amount by weight of the swellable hydrophilic carrier is in the range of about 0.7 to about 4.

The present invention provides a composition suitable for sublingual or buccal tablets for the relatively slow release of water soluble drugs. Further, this invention provides ways of varying the composition to adjust drug release for optimal absorption, thereby increasing the bioavailability of the drug. Controlled drug release of the water soluble drug can be used to enhance the therapeutic benefit of the drug while at the same time reducing or eliminating its undesirable side effects.

This invention as described is particularly applicable to drugs such as apomorphine. The practice of this invention using apomorphine is desired since increasing the bioavailability of this drug is useful in the treatment of psychogenic impotence. Further, this invention allows for the successful use of this drug without major side effects occurring in the impotent male which are extremely undesirable and have, in the past, prevented apomorphine from becoming a useful therapy for this condition.

The practice of this invention using apomorphine can be applied the treatment of severe motor fluctuations in Parkinson's disease as well.

DETAILED DESCRIPTION OF THE PREFERRED EMBODIMENTS

The present invention provides formulations for controlled release tablets in a time course suitable for sublingual or buccal drug delivery. For the present compositions, 90 percent by weight of the apomorphine present is released in a water solution over a time period in the range of more than about 25 minutes to about 300 minutes. In the ensuing specification and claims, the release time is referred to as a $T_{90}$ value. That is, the present compositions have a $T_{90}$ value in the range of more than about 25 minutes to about 300 minutes.

Tablets are made of a water-insoluble carrier whose porous structure is filled, coated, or covered by the active ingredient; an osmotic agent; and if necessary, a stabilizing adjuvant. The above drug-loaded carrier system is then mixed with a water dispersible polymer and subjected to direct compression into a tablet. Upon contact of the tablets of this invention with biological fluids, such as saliva, and with the aid of the osmotic agent, two opposing phenomena occur simultaneously.

1. Gelling of the water dispersible polymer which slows the drug diffusion from the tablet matrix.

2. Swelling of the water-insoluble carrier providing more surface area for further fluid penetration with aqueous channel formation, leading to a faster diffusion or release of the active ingredient.

For example, tablets containing microcrystalline cellulose as a water insoluble carrier and mannitol as the osmotic agent (approximately 1:1 ratio w/w) and various water soluble nonionic polymers provided a controlled release rate of apomorphine HCl suitable for sublingual and/or buccal delivery.

It was further discovered that an anionic polymer such as polyacrylate, sodium alginate or anionic gelatin provided an exceptional controlled rate of drug release. The exceptionally low rate of drug release from tablets containing anionic water dispersible polymers is due to the presence of water soluble organic acids present in these tablet matrices. These organic acids react with the anionic water dispersible polymers in the presence of water or biological fluids such as saliva, to produce a more structured gel of the polymer (in situ-made unionized form of the anionic polymers).

The treatment of psychogenic impotence can be achieved by the practice of this invention. The practice of this art entails the administration of the apomorphine sublingual tablet preferably about 15 to about 45 minutes prior to sexual activity.

In general, a preferred dosage form contains about 2 milligrams to about 40 milligrams of apomorphine. For treating psychogenic impotence a preferred dosage form contains about 2 milligrams to about 10 milligrams of apomorphine. For treating Parkinson's disease a preferred dosage form contains about 10 milligrams to about 40 milligrams of apomorphine.

Apomorphine can be represented by the formula:

and exists in a free base form or as an acid addition salt. For the purposes of the present invention, apomorphine hydrochloride is preferred; however, other pharmacologically acceptable moieties thereof can be utilized as sufficiently. The term "apomorphine" as used herein includes the free base form of this compound as sufficiently as the pharmacologically acceptable acid addition salts thereof. In addition to the hydrochloride salt, other acceptable acid addition salts are the hydrobromide, the hydroiodide, the bisulfate, the phosphate, the acid phosphate, the lactate, the citrate, the tartrate, the salicylate, the succinate, the maleate, the gluconate, and the like.

Illustrative preferred sublingual dosage forms are set forth in the Examples 1–17, 20 and 21. Other formulae are possible prepared from other pharmaceutical ingredients as shown in Table 1 below.

TABLE 1

Suitable Components

| Swellable Hydrophilic Carriers | Osmotic Agents | Polymers |
| --- | --- | --- |
| ethyl cellulose | mannitol | hydroxypropyl cellulose |
| fumed silica | sorbitol | hydroxymethyl cellulose |
| Cross-linked PVP | lactose | gelatin |
| microcrystalline cellulose | glucose | carboxymethyl cellulose |
| Silica | fructose | gum tragacanth |
| Dicalcium Phosphate | sucrose | gum acacia |
| Calcium Carbonate | mono & di-saccharides | guar gum |
| | glycerin | sodium alginate |
| | polyelectolytes | polymethacrylic acid |
| | urea | polyacrylic acid |
| | sodium chloride | salts of polysilicic acid |
| | potassium chloride | polylactic acid |
| | organic & inorganic salts | water soluble starch |
| | | carbomers |
| | | polycarbophils |
| | | polyvinyl alcohol |
| | | polyethylene glycol |
| | | alkyloxy block copolymers |
| | | methyl cellulose |
| | | polysorbates |
| | | polymaleic acid |

The compositions described in Examples 1–18 allow for the release and control of mucosal absorption of the apomorphine permitting the desired plasma levels at the concentration maximum to be achieved. The composition affords other significant attributes as well. Apomorphine is an unstable chemical moiety in the presence of light, and oxygen. The formulation composition affords the chemical moiety unique stability as measured by continuous testing of the preparations. Further, hydroxymethylcellulose in combination with microcrystalline and mannitol perform as a matrix where in the presence of saliva, swell and allow for the sufficiently controlled release of the apomorphine, thus controlling the plasma concentration of the drug. Further, these formulae can be flavored in addition to a variety of sweeteners to overcome the unpleasant taste and bitter after-taste of this drug. The purpose of the flavoring agents is two fold. First: the formulation flavored with a mild mint flavor affords to the desirability of the sublingual tablet (which can remain under the tongue for up to 10 minutes). Second: the use of mint type flavors can attenuate some of the local emesis type receptors located in the oral/pharyngeal region of the patient. This is desirable because localized stimulation of the receptors by apomorphine can exacerbate the nausea associated with this drug.

Formulation stability and the stabilizing effect of the tablet matrix are extremely valuable for the practice of this invention. Apomorphine hydrochloride is known to be unstable in the presence of air and light. Apomorphine rapidly oxidizes in a variety of quinone, diquinone compounds when this drug is exposed for relatively short periods of time to air and light. These diquinones so formed can and do dimerize producing highly conjugated compounds which appear in the product as visible color. Thus, not only is the potency of the apomorphine at risk, but the overall product elegance can be violated making the product unacceptable as a drug product.

To overcome this problem, the tablet matrix has been developed furnishing the apomorphine with significant stability. This is accomplished by first the composition of the tablet, and the means in which it is prepared. Significant to this invention is the process by which the ingredients are added to prepare the tablets. The procedure used in adding the components of the drug product represent a physical means of enveloping the drug substance with an appropriate barrier reducing the oxygen tension at the physical location of the drug substance contained. Upon compression of the formulation into the drug product, i.e., the sublingual tablet, the drug substance is well protected from ambient oxygen affording this product shelf stability and elegance.

The following examples are intended to illustrate, but not limit, the present invention.

EXAMPLE 1

Direct Compression Composition A

Compositions were mixed from dry ingredients and formed into tablets by the direct compression method. Composition A was prepared by weighing the amounts of the ingredients listed in Table 2, below. Each ingredient was passed through an appropriate sized (30 mesh) screen. The apomorphine HCl, ascorbic acid, aspartame, D&C yellow 10 Lake, and the citric acid were placed into a blender and blended for 5 minutes. Hydroxypropyl methylcellulose (Methocel E4M, Premium), the water dispersible polymer, was added to the blender and mixing was continued for an additional 5 minutes. Microcrystalline cellulose (Avicel PH102) was then added to the blender and mixing was continued for an additional 5 minutes. Next, the mannitol was added to the blender and mixed for an additional 5 minutes. Finally, the magnesium stearate was added to the blender and mixed for an additional 2 minutes to yield a final powder mix. The final powder mix was transferred to a suitable tableting machine equipped with the appropriate sized tooling and compressed into tablets.

Figure 1:
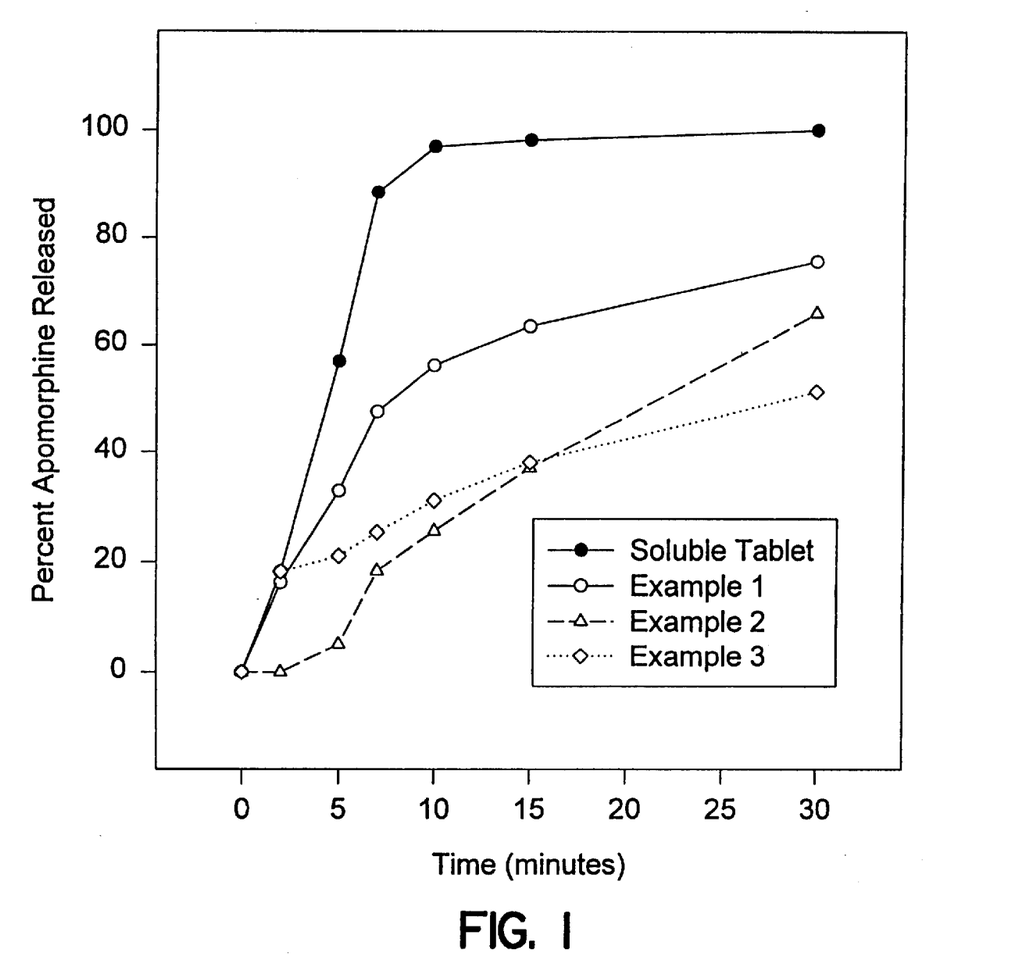
FIG. 1 is a graph of the dissolution of the direct compression apomorphine compositions of Examples 1, 2, and 3 compared to that of a commercially available soluble tablet.

Dissolution was measured using USP Type II apparatus (USP XXIII) stirred at 30 rpm. The dissolution medium was 700 ml of distilled water at 37 degrees Celsius. Apomorphine released into the medium was analyzed by high pressure liquid chromatography (HPLC). Dissolution kinetic ($K_{diss}$) constants were calculated assuming first-order release kinetics. The tablets prepared were compared against a commercial soluble apomorphine HCl tablet (Apomorphine HCl tablet 6 mg, Lot #1000AP, Anpro Products, Arcadia, Calif.) for dissolution characterization. The results are presented in Tables 5 and 7, below, and in FIG. 1.

Composition A dissolved and released apomorphine relatively slowly compared to the commercial soluble tablet.

EXAMPLE 2
Direct Compression Composition B

Composition B was prepared by weighing the amounts of the ingredients listed in Table 2, below, mixing the ingredients and forming tablets by the direct compression method as described in Example 1. The water dispersible polymer used was hydroxypropyl methylcellulose. Dissolution of the tablets was measured as described in Example 1. The results are presented in Tables 5 and 7, below, and in FIG. 1.

Composition B dissolved and released apomorphine slower than either the commercial soluble tablet or Composition A.

EXAMPLE 3
Direct Compression Composition C

Composition C was prepared by weighing the amounts of the ingredients, listed in Table 2, below, mixing the ingredients and forming tablets by the direct compression method as described in Example 1. The water dispersible polymer used was hydroxypropyl methylcellulose. Dissolution of the tablets was measured as described in Example 1. The results are presented in Tables 5 and 7, below, and in FIG. 1.

Composition C dissolved and released apomorphine initially at the same rate as the commercial soluble tablet and Composition A. However, the rate of apomorphine released slowed after 5 minutes, and less than 50% of the apomorphine was released after 30 minutes.

TABLE 2

Direct Compression Compositions

| Ingredient (mg/tablet) | A | B | C |
| --- | --- | --- | --- |
| Apomorphine HCl, USP | 4.00 | 6.00 | 8.00 |
| Ascorbic Acid, USP | 3.00 | 3.00 | 3.00 |
| Citric Acid, Anhydrous, NF | 2.00 | 2.00 | 2.00 |
| Microcrystalline Cellulose, NF (Avicel PH102) | 22.70 | 22.70 | 22.70 |
| Magnesium Stearate, NF | 1.20 | 1.20 | 1.20 |
| Hydroxypropyl methylcellulose (Methocel E4M Premium, NF) | 5.00 | 5.00 | 5.00 |
| D&C Yellow 10 Aluminum Lake, NF | 0.10 | 0.10 | 0.10 |
| Aspartame, USP | 1.00 | 1.00 | 1.00 |
| Mannitol, USP, powder | 21.00 | 19.00 | 17.00 |
| TOTAL, mg/tablet | 60.00 | 60.00 | 60.00 |

EXAMPLE 4
Wet Granulation Composition D

Compositions were mixed and formed into tablets by the wet granulation method. Composition D was prepared from the ingredients listed in Table 3, below. The water dispersible polymer used was a carbomer, Carbopol 974P. Each ingredient was weighed as indicated. A solution containing apomorphine HCl, citric acid, and ascorbic acid was prepared by dissolving the ingredients into a mixture of equal volumes of purified water and ethanol, USP. The solution was warmed slightly, mannitol was added. The solution was mixed until clear, then absorbed onto the microcrystalline cellulose to form a mass. The mass was mixed in a stainless steel pan until uniform. The mass was granulated by screening through a #8 mesh screen and then dried at about 60 to about 70 degrees Celsius for about 4 hours. The mass was mixed periodically during this drying step.

The resultant dried granules were passed through a 32 mesh screen. The appropriate polymers and aspartame were blended with the dried granules for a period of about 5 minutes using a twin shell V-shaped blender. At the end of the blending cycle magnesium stearate was added to the blender and the blending was continued for an additional 2 minutes to produce a final mix.

The final mix was removed from the blender and fed into a Stoke's single punch tablet press fitted with fitted with biconvex 7/32" diameter tooling for tablet preparation. Tablets were prepared at various compression forces, yielding tablets of different hardnesses.

Figure 2:
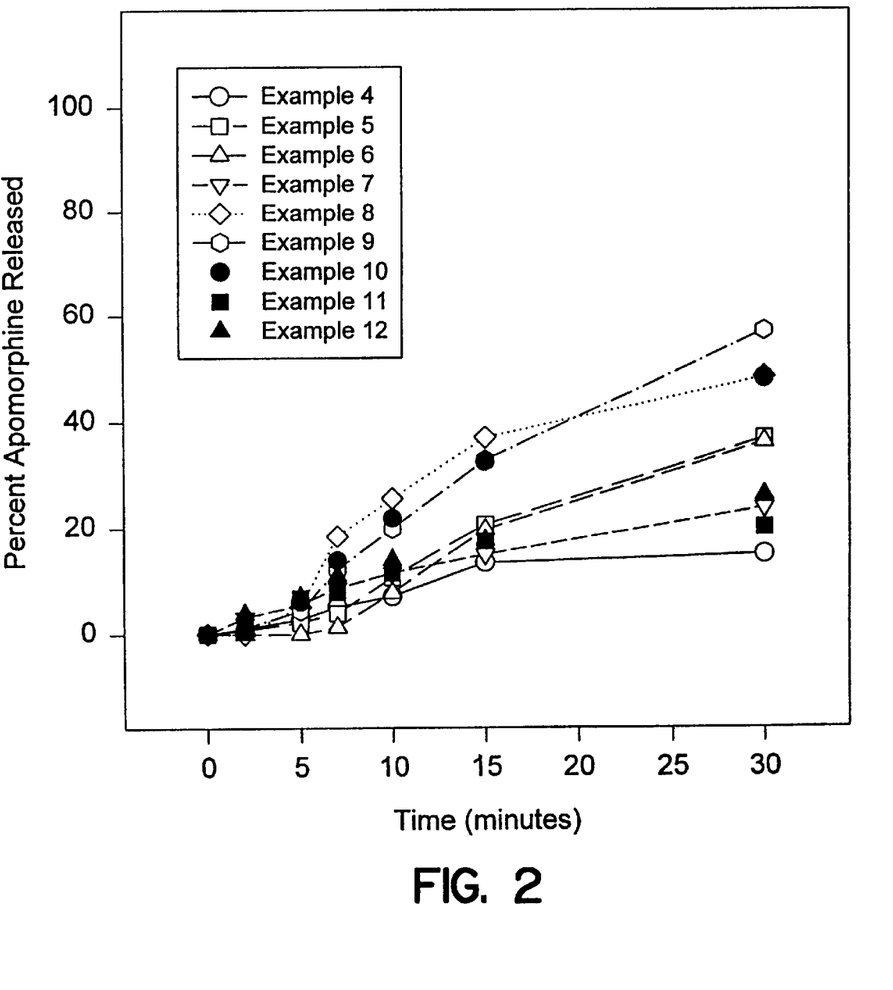
FIG. 2 is a graph of the dissolution of wet granulation apomorphine compositions.

Dissolution of the tablets was measured as described in Example 1. The results are presented in Tables 6 and 7, below, and in FIG. 2.

EXAMPLE 5
Wet Granulation Composition E

Composition E was prepared by weighing the amounts of the ingredients, listed in Table 3, below, mixing the ingredients and forming tablets by the wet granulation method as described in Example 4. The water dispersible polymer used was sodium alginate. Dissolution of the tablets was measured as described in Example 1. The results are presented in Tables 6 and 7, below, and in FIG. 2.

EXAMPLE 6
Wet Granulation Composition F

Composition F was prepared by weighing the amounts of the ingredients, listed in Table 3, below, mixing the ingredients and forming tablets by the wet granulation method as described in Example 4. The water dispersible polymer used was sodium alginate. Dissolution of the tablets was measured as described in Example 1. The results are presented in Tables 6 and 7, below, and in FIG. 2.

EXAMPLE 7
Wet Granulation Composition G

Composition G was prepared by weighing the amounts of the ingredients, listed in Table 3, below, mixing the ingredients and forming tablets by the wet granulation method as described in Example 4. The water dispersible polymer used was gelatin. Dissolution of the tablets was measured as described in Example 1. The results are presented in Tables 6 and 7, below, and in FIG. 2.

EXAMPLE 8
Wet Granulation Composition H

Composition H was prepared by weighing the amounts of the ingredients, listed in Table 3, below, mixing the ingredients and forming tablets by the wet granulation method as described in Example 4. The water dispersible polymer used was carboxymethyl cellulose. Dissolution of the tablets was measured as described in Example 1. The results are presented in Tables 6 and 7, below, and in FIG. 2.

EXAMPLE 9
Wet Granulation Composition I

Composition I was prepared by weighing the amounts of the ingredients, listed in Table 3, below, mixing the ingredients and forming tablets by the wet granulation method as described in Example 4. The water dispersible polymer used was gum tragacanth. Dissolution of the tablets was measured as described in Example 1. The results are presented in Tables 6 and 7, below, and in FIG. 2.

Composition L was prepared by weighing the amounts of the ingredients, listed in Table 4, below, mixing the ingredients and forming tablets by the wet granulation method as described in Example 4. The water dispersible polymer used was polyethylene glycol. Dissolution of the tablets was measured as described in Example 1. The results are presented in Tables 6 and 7, below, and in FIG. 2.

TABLE 3

Wet Granulation Compositions

| INGREDIENT (mg/tablet) | D | E | F | G | H | I | J |
|---|---|---|---|---|---|---|---|
| Apomorphine HCl, USP | 6.00 | 6.00 | 6.00 | 6.00 | 6.00 | 6.00 | 6.00 |
| Ascorbic Acid, USP | 3.00 | 3.00 | 3.00 | 3.00 | 3.00 | 3.00 | 3.00 |
| Citric Acid, Anhydrous, NF | 2.00 | 2.00 | 2.00 | 2.00 | 2.00 | 2.00 | 2.00 |
| Microcrystalline Cellulose, NF (Avicel PH102) | 40.00 | 40.00 | 40.00 | 40.00 | 40.00 | 40.00 | 40.00 |
| Magnesium Stearate, NF | 1.00 | 1.00 | 1.00 | 1.00 | 1.00 | 1.00 | 1.00 |
| Aspartame, USP | 1.00 | 1.00 | 1.00 | 1.00 | 1.00 | 1.00 | 1.00 |
| Mannitol, USP, powder | 42.00 | 42.00 | 42.00 | 42.00 | 42.00 | 42.00 | 42.00 |
| Carbomer (Carbopol 974P) | 10.00 | — | — | — | — | — | — |
| Sodium Alginate | — | 5.00 | 10.00 | — | — | — | — |
| Gelatin, NF | — | — | — | 10.00 | — | — | — |
| Sodium Carboxymethyl Cellulose | — | — | — | — | 10.00 | — | — |
| Gum Tragacanth, NF | — | — | — | — | — | 10.00 | — |
| Hydroxypropyl methylcellulose (Methocel E4M, NF) | — | — | — | — | — | — | 10.00 |
| TOTAL, mg/tablet | 105.00 | 100.00 | 105.00 | 105.00 | 105.00 | 105.00 | 105.00 |

EXAMPLE 10
Wet Granulation Composition J

Composition J was prepared by weighing the amounts of the ingredients, listed in Table 3, above, mixing the ingredients and forming tablets by the wet granulation method as described in Example 4. The water dispersible polymer used was hydroxylpropyl methylcellulose. Dissolution of the tablets was measured as described in Example 1. The results are presented in Tables 6 and 7, below, and in FIG. 2.

EXAMPLE 11
Wet Granulation Composition K

Composition K was prepared by weighing the amounts of the ingredients, listed in Table 4, below, mixing the ingredients and forming tablets by the wet granulation method as described in Example 4. The water dispersible polymer used was polyvinyl pyrrolidone. Dissolution of the tablets was measured as described in Example 1. The results are presented in Tables 6 and 7, below, and in FIG. 2.

EXAMPLE 12
Wet Granulation Composition L

EXAMPLE 13
Wet Granulation Composition M

Composition M was prepared by weighing the amounts of the ingredients, listed in Table 4, below, mixing the ingredients and forming tablets by the wet granulation method as described in Example 4. The water dispersible polymer used was sodium alginate. Dissolution of the tablets was measured as described in Example 1. The results are presented in Table 7, below.

EXAMPLE 14
Wet Granulation Composition N

Composition N was prepared by weighing the amounts of the ingredients, listed in Table 4, below, mixing the ingredients and forming tablets by the wet granulation method as described in Example 4. The water dispersible polymer used was a carbomer (Carbopol 974P). Dissolution of the tablets was measured as described in Example 1. The results are presented in Table 7, below.

TABLE 4

Other Wet Granulation Compositions

| INGREDIENT (mg/tablet) | K | L | M | N | O | P | Q |
|---|---|---|---|---|---|---|---|
| Apomorphine HCl, USP | 6.00 | 6.00 | 4.00 | 4.00 | 8.00 | 6.00 | 4.00 |
| Ascorbic Acid, USP | 3.00 | 3.00 | 3.00 | 3.00 | 3.00 | 3.00 | 3.00 |
| Citric Acid, Anhydrous, NF | 2.00 | 2.00 | 2.00 | 2.00 | 2.00 | 2.00 | 2.00 |
| Microcrystalline Cellulose, NF (Avicel PH 102) | 40.00 | 40.00 | 40.00 | 40.00 | 40.00 | 40.00 | 40.00 |
| Magnesium Stearate, NF | 1.00 | 1.00 | 1.00 | 1.00 | 1.00 | 1.00 | 1.00 |
| Aspartame, USP | 1.00 | 1.00 | 1.00 | 1.00 | 1.00 | 1.00 | 1.00 |
| Mannitol, USP, powder | 42.00 | 42.00 | 42.00 | 42.00 | 42.00 | 42.00 | 42.00 |
| Polyvinyl pyrrolidone | 10.00 | — | — | — | — | — | — |
| Polyethylene glycol | — | 10.00 | — | — | — | — | — |
| Sodium Alginate | — | — | 10.00 | — | 10.00 | — | 10.00 |
| Carbomer (Carbopol 974P) | — | — | — | 10.00 | — | — | — |

TABLE 4-continued

Other Wet Granulation Compositions

| INGREDIENT (mg/tablet) | K | L | M | N | O | P | Q |
|---|---|---|---|---|---|---|---|
| Mint Flavor | — | — | — | — | — | — | 0.2 |
| Ascorbic acid palmitate | — | — | — | — | — | 10.00 | — |
| TOTAL, mg/tablet | 105.00 | 105.00 | 103.00 | 103.00 | 107.00 | 105.00 | 103.20 |

EXAMPLE 15
Wet Granulation Composition O

Composition O was prepared by weighing the amounts of the ingredients, listed in Table 4, above, mixing the ingredients and forming tablets by the wet granulation method as described in Example 4. The water dispersible polymer used was sodium alginate. Dissolution of the tablets was measured as described in Example 1. The results are presented in Table 7, below.

EXAMPLE 16
Wet Granulation Composition P

Composition P was prepared by weighing the amounts of the ingredients, listed in Table 4, above, mixing the ingredients and forming tablets by the wet granulation method as described in Example 4. The water dispersible polymer used was ascorbic acid palmitate. Dissolution of the tablets was measured as described in Example 1. The results are presented in Table 7, below.

EXAMPLE 17
Wet Granulation Composition Q

Composition Q was prepared by weighing the amounts of the ingredients, listed in Table 4, above, mixing the ingredients and forming tablets by the wet granulation method as described in Example 4. The water dispersible polymer used was sodium alginate. Dissolution of the tablets was measured as described in Example 1. The results are presented in Table 7, below.

EXAMPLE 18
Comparison of Dissolution Properties

The dissolution times and constants for composition were determined as described in Example 1. The results are presented in Tables 5, 6 and 7, below, and in FIGS. 1 and 2.

TABLE 5

Dissolution of Direct Compression Compositions

| Time (minutes) | A | B | C | SOLUBLE TABLET |
|---|---|---|---|---|
| 0 | 0.00 | 0.00 | 0.00 | 0.00 |
| 2 | 16.32 | 0.00 | 8.90 | 18.24 |
| 5 | 32.81 | 5.14 | 21.08 | 56.97 |
| 7 | 47.54 | 18.38 | 25.37 | 88.47 |
| 10 | 56.20 | 25.59 | 31.05 | 97.00 |
| 15 | 63.51 | 36.96 | 38.02 | 98.22 |
| 30 | 75.53 | 65.88 | 51.26 | 100.00 |

Table 5 shows the percent apomorphine HCl released from the tablet matrix. These data demonstrate the ability of the direct compression tablet method to produce a sufficiently controlled release of the drug as compared with the dissolution time for the soluble tablet. The rate constants of apomorphine release and the hardness for each tablet for the three examples compared with the soluble tablet are shown in Table 7, below. These data show a significant difference in the apomorphine release characteristics for the dry compression sublingual tablets prepared by this invention.

Sublingual tablets prepared by the wet granulation method described in Examples 4 through 12 were compared for their dissolution characteristics under identical conditions. The results are given in Table 6, below.

TABLE 6

Dissolution of Wet Granulation Compositions

| Time (Minutes) | D | E | F | G | H | I | J | K | L |
|---|---|---|---|---|---|---|---|---|---|
| 0 | 0.00 | 0.00 | 0.00 | 0.00 | 0.00 | 0.00 | 0.00 | 0.00 | 0.00 |
| 2 | 1.05 | 0.71 | 0.00 | 3.10 | 0.00 | 1.11 | 0.63 | 2.49 | 3.81 |
| 5 | 2.73 | 2.13 | 0.00 | 5.55 | 5.14 | 4.38 | 6.15 | 6.77 | 7.07 |
| 7 | 5.14 | 3.93 | 1.29 | 8.71 | 18.38 | 12.11 | 13.78 | 7.91 | 10.93 |
| 10 | 7.16 | 10.66 | 7.79 | 11.44 | 25.59 | 19.85 | 21.84 | 11.51 | 13.87 |
| 15 | 13.38 | 20.60 | 19.62 | 14.90 | 36.96 | 32.73 | 32.42 | 17.42 | 17.64 |
| 30 | 14.97 | 36.80 | 36.08 | 23.78 | 48.23 | 56.93 | 48.00 | 20.08 | 26.06 |

The dissolution data were used to calculate the dissolution constant for each formula, which is shown, along with tablet hardness, in Table 7, below.

These findings demonstrate the ability of anionic polymers, synthetic and natural occurring, can be used in the practice of this invention to produce dynamic characteristics to the mechanism for releasing apomorphine from the tablet matrix. The hardness of the finished tablet is not a determinant of the release characteristics for the preparation.

TABLE 7

Properties of Tablets

| Composition | $K_{diss}$ | $T_{50}$ | $T_{90}$ | $r^2$ | Hardness, $k_p$ |
|---|---|---|---|---|---|
| A | 0.075 | 9.24 | 30.56667 | 0.92 | 2.91 |
| B | 0.0387 | 17.90698 | 59.43152 | 0.9653 | 2.73 |
| C | 0.0355 | 19.52113 | 64.78873 | 0.8901 | 2.74 |
| D | 0.0085 | 81.52941 | 270.5882 | 0.9364 | 15.2 |
| E | 0.0124 | 55.8871 | 185.4839 | 0.8163 | 13.2 |
| F | 0.0104 | 86.63462 | 221.1538 | 0.6812 | 11.2 |
| G | 0.0115 | 60.26087 | 200 | 0.9687 | 11.7 |
| H | 0.0387 | 17.90698 | 59.43152 | 0.9653 | 9.8 |
| I | 0.0231 | 30 | 99.5671 | 0.8971 | 11.3 |
| J | 0.0241 | 28.75519 | 95.435682 | 0.9319 | 7.2 |
| K | 0.0126 | 55 | 182.5397 | 0.9934 | 11.9 |
| L | 0.014 | 49.5 | 164.2867 | 0.9475 | 7.2 |
| M | 0.0256 | 27.17647 | 90.19608 | 0.946 | 9.6 |
| N | 0.0045 | 154 | 511.1111 | 0.948 | 8.5 |
| O | 0.0255 | 27.17647 | 90.19608 | 0.96 | 8.7 |
| P | 0.0187 | 37.05882 | 122.9947 | 0.991 | 6.0 |
| Soluble Tablet | 0.286 | 2.423077 | 8.041958 | 0.9087 | — |

EXAMPLE 19
Clinical Studies

A clinical study, "Apomorphine Hydrochloride, USP Sublingual Tablet Escalating Dose Tolerance Study for the Treatment of Psychogenic Male Erectile Dysfunction (MED)" examined the effects sublingual tablets in a multicenter, double-blind, placebo-controlled escalating dose tolerance outpatient study. All subjects received both placebo and apomorphine.

After a baseline screening evaluation, the study was divided into three phases. In the first phase, qualified subjects reported for the placebo phase (Visit 1) within 1 week of the baseline screening evaluation. On Day 8, subjects began the second phase, comprising 4 weekly treatments (Visits 2–5). At the end of Visit 5, subject began the third phase, a 5 week home treatment, which included Visit 6. The final termination visit, Visit 7, occurred at the end of this period. The study was designed to have a total duration of about 6 months, with each subject participating for 11 weeks.

Subjects were consenting males between 18 and 65 years of age who had psychogenic erectile dysfunction as defined by the protocol inclusion/exclusion criteria. Eighty seven potential subjects did not qualify at the basic screening stage. Fifty two subjects entered the study and 36 subjects completed the study.

The study medications were apomorphine HCl in sublingual tablets at three dose levels: 4 mg (Composition A), 6 mg (Composition B) and 8 mg (Composition C), as well as matching placebo tablets.

After the baseline visit, the subjects received study medication at doses that escalated per subject tolerance at each subsequent treatment phase visit. The tablets were given sublingually and allowed to absorb over a period of at least about 15 minutes.

Safety was assessed by changes in physical examination, vital signs, laboratory tests and occurrence of adverse events. Subjects were evaluated for adverse events and vital sign changes at each visit after the screening visit. Vital signs and laboratory parameters defined in the study protocol were assessed at the baseline visit and Visit 7.

Efficacy was assessed at Visits 1–7. One primary efficacy variable was maximum increase in penile circumference and rigidity in response to erotic and neutral videotapes, as measured by the RigiScan instrument and expressed as a RigiScan number. Another primary efficacy variable was the response to subject questionnaires designed separately for home and clinic use.

Figure 3:
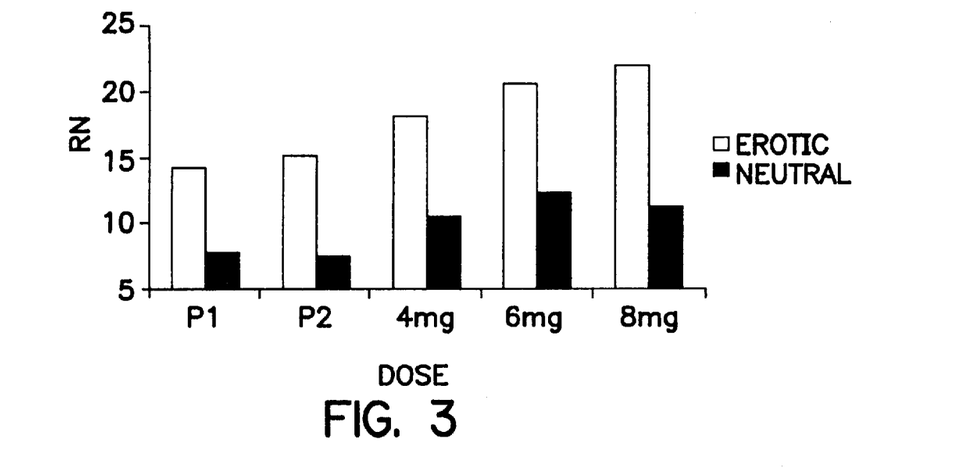
FIG. 3 shows the RigiScan number results of treatment of patients with apomorphine compositions.
Figure 4:
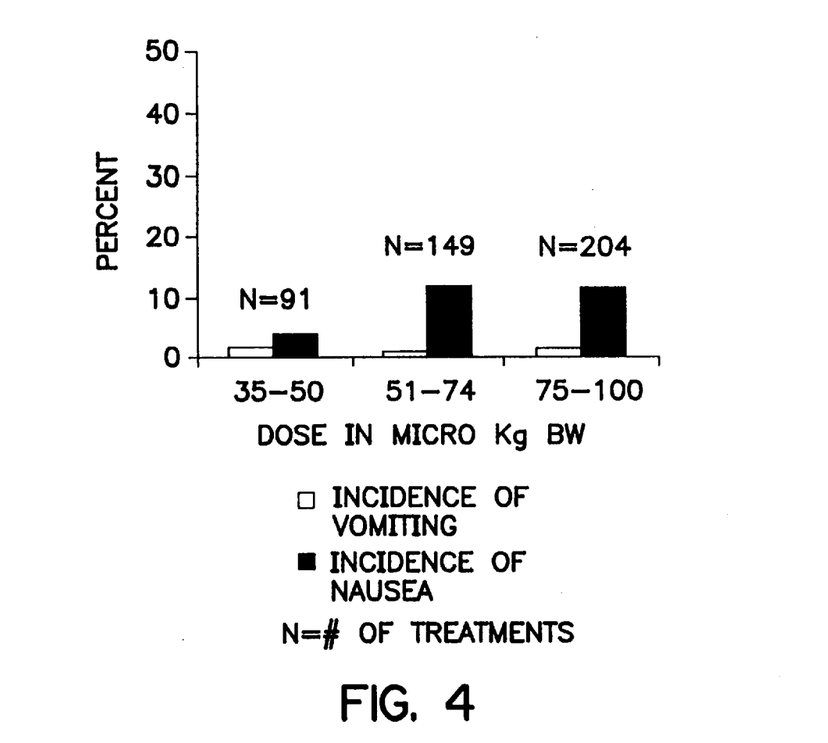
FIG. 4 shows the occurrence of nausea and vomiting by number of treatments, expressed as percent of subjects, dosage expressed per kilograms body weight.
Figure 5:
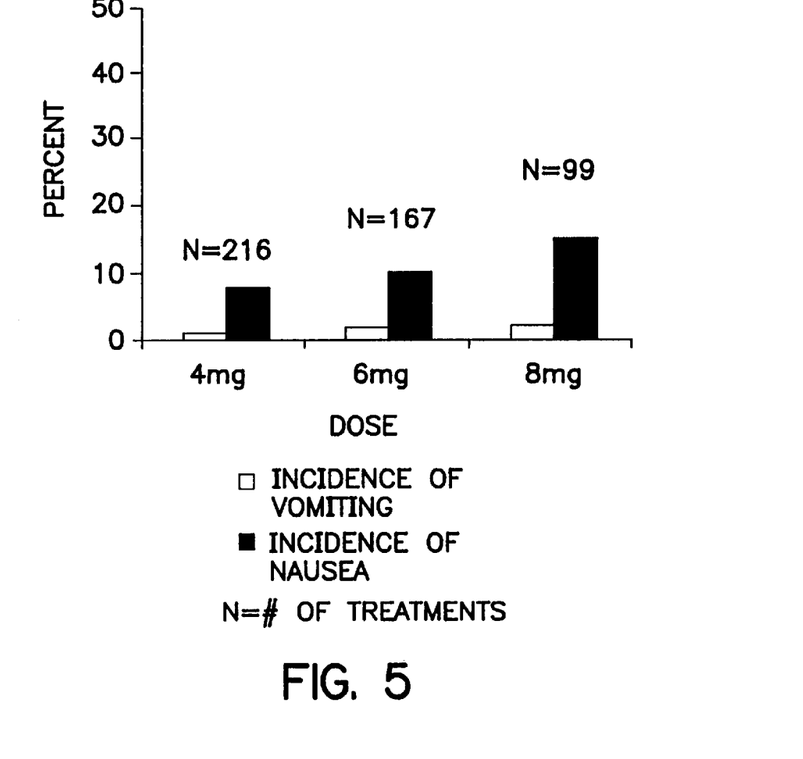
FIG. 5 shows the incidence of nausea and vomiting by number of treatments, expressed as percent of subjects, dosage expressed as milligrams of apomorphine in the composition.
Figure 6:
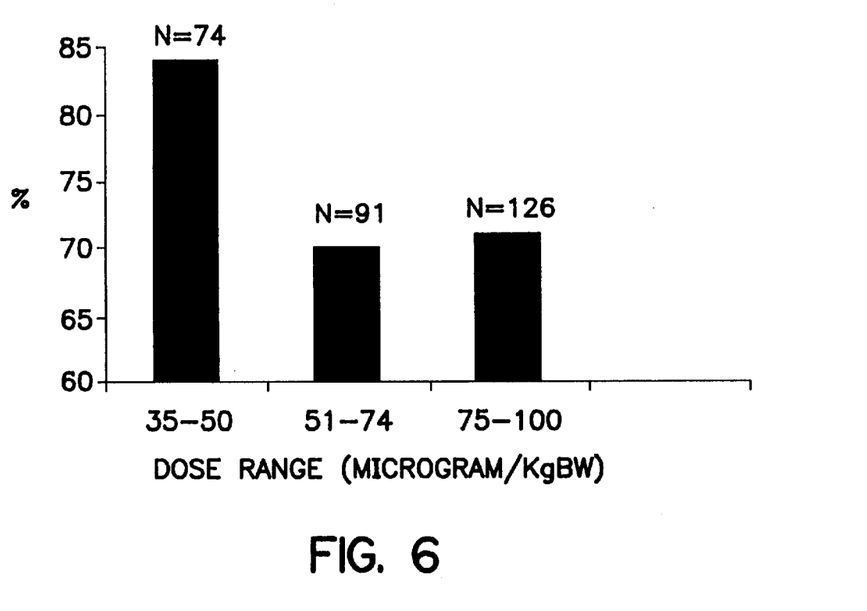
FIG. 6 shows the success rate by number of treatments, expressed as percent of subjects, dosage expressed per kilograms body weight.
Figure 7:
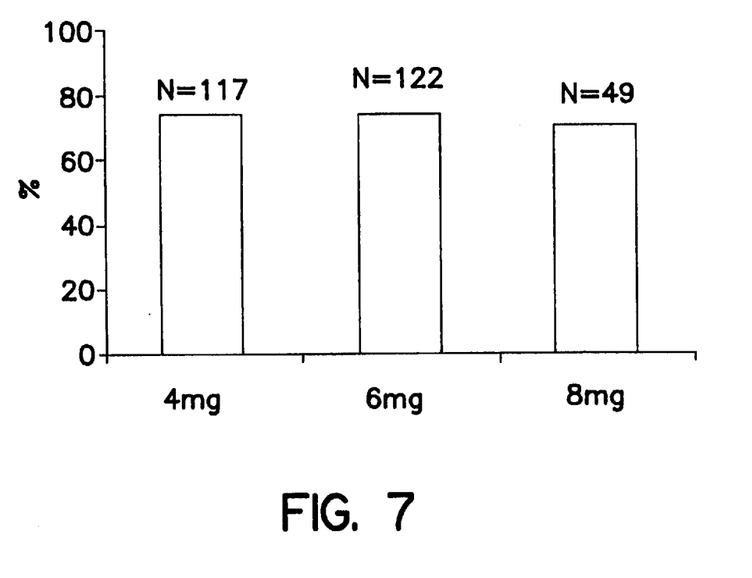
FIG. 7 shows the success rate by number of treatments, expressed as percent of subjects, dosage expressed as milligrams of apomorphine in the composition.

The apomorphine compositions produced a dose-dependent increase in RigiScan number elicited by erotic videotapes, while the increase in RigiScan number elicited by neutral videotapes was not dose-dependent (FIG. 3). The incidence of nausea and vomiting was less than 3% nausea and 15% vomiting at the highest dosage levels and less at lower levels (FIGS. 4 and 5). The success rate reported after the take-home phase was higher at lower dosages expressed per body weight (FIG. 6). There was no apparent effect of the particular composition on success rate (FIG. 7).

EXAMPLE 20
Direct Compression Composition R

Figure 8:
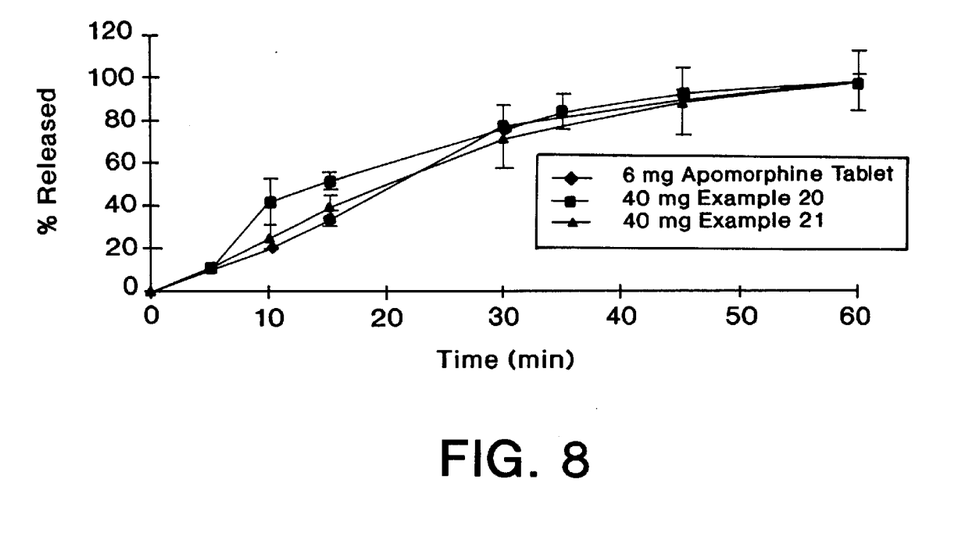
FIG. 8 is a graph of the dissolution of the direct compression apomorphine compositions of Examples 20 and 21.

Composition R was prepared by weighing the amounts of the ingredients, listed in Table 8, below, mixing the ingredients and forming tablets by the direct compression method as described in Example 1. The water dispersible polymer used was hydroxypropyl methylcellulose. Dissolution of the tablets was measured as described in Example 1. The results are presented in FIG. 8. The values of $T_{90}$ obtained were in the range 35–45 minutes.

EXAMPLE 21
Direct Compression Composition S

Composition S was prepared by weighing the amounts of the ingredients, listed in Table 8, below, mixing the ingredients and forming tablets by the direct compression method as described in Example 1. The water dispersible polymer used was hydroxypropyl methylcellulose. Dissolution of the tablets was measured as described in Example 1. The results are presented in FIG. 8. The values of $T_{90}$ obtained were in the range 30–45 minutes.

TABLE 8

Direct Compression Compositions

| Ingredient (mg/tablet) | R | S |
| --- | --- | --- |
| Apomorphine HCl, USP | 40.0 | 40.0 |
| Ascorbic Acid, USP | 7.5 | 8.4 |
| Citric Acid, Anhydrous, NF | 5.0 | 5.6 |
| Microcrystalline Cellulose, NF (Avicel PH102) | 57.0 | 39.2 |
| Magnesium Stearate, NF | 3.0 | 2.8 |
| Hydroxypropyl methylcellulose (Methocel E4M Premium, NF) | 12.5 | 8.4 |
| Turquoise Lake | 3.0 | 2.8 |
| Aspartame, USP | 2.5 | 2.8 |
| Mannitol, USP, powder | 19.5 | 30.0 |
| TOTAL, mg/tablet | 150.0 | 140.0 |

The foregoing is intended to be illustrative of the present invention, but not limiting. Numerous variations and modifications may be effected without departing from the true spirit and scope of the invention.

We claim:

1. A composition providing a relatively slow release of water-soluble drugs by sublingual route and consisting essentially of:

a water-soluble drug which is a member of the group consisting of apomorphine hydrochloride, albuterol sulfate, timolol maleate, verapamil hydrochloride and naloxone hydrochloride;

an osmotic agent;

a swellable hydrophilic carrier;

and a water dispersible polymer;

the composition having a $T_{90}$ value in the range of more than about 25 to about 300; and the composition having the ratio of the amount by weight of the osmotic agent to the amount by weight of the swellable hydrophilic carrier in the range of about 0.3 to about 4.

2. The composition of claim 1 containing from about 2 milligrams to about 40 milligrams of the water-soluble drug.

3. The composition of claim 1 wherein the ratio of the amount by weight of the osmotic agent to the amount by weight of the swellable hydrophilic carrier is less than about 4.

4. The composition of claim 1 containing from about 10 milligrams to about 40 milligrams of the water-soluble drug.

5. The composition of claim 1 wherein the osmotic agent is selected from the group consisting of sugars, glycerin, polyelectrolytes, organic salts and inorganic salts.

6. The composition of claim 1 wherein the osmotic agent is mannitol.

7. The composition of claim 1 wherein the swellable hydrophilic carrier is selected from the group consisting of ethyl cellulose, microcrystalline cellulose, cross-linked polyvinyl pyrrolidone, dicalcium phosphate, calcium carbonate and silica.

8. The composition of claim 1 wherein the swellable hydrophilic carrier is microcrystalline cellulose.

9. The composition of claim 1 wherein the water dispersible polymer is selected from the group consisting of methylcellulose, carboxymethyl cellulose, hydroxymethylcellulose, hydroxypropyl methylcellulose, alginates, gelatin, guar gum, gum tragacanth, gum acacia, polyacrylic acid, polymethacrylic acid, polysilicic acid, polylactic acid, polymaleic acid, polyvinyl alcohol, polyethylene glycol, polyvinyl pyrrolidone, nonionic blocked polymers, carbomers, polycarbophils, and water soluble starches.

10. The composition of claim 1 wherein the water dispersible polymer is methylcellulose.

11. The composition of claim 1 wherein the water dispersible polymer is carboxymethylcellulose.

12. The composition of claim 1 wherein the water dispersible polymer is hydroxypropyl methylcellulose.

13. The composition of claim 1 wherein the water dispersible polymer is sodium alginate.

14. The composition of claim 1 wherein the water dispersible polymer is gum tragacanth.

15. The composition of claim 1 wherein the water dispersible polymer is polyvinyl pyrrolidone.

16. The composition of claim 1 wherein the water dispersible polymer is a carbomer.

17. The composition of claim 1 wherein the water dispersible polymer is polyethylene glycol.

18. The composition of claim 1 wherein the ater dispersible polymer is gelatin.

19. The composition of claim 1 wherein the water dispersible polymer is ascorbic acid palmitate.

20. The composition of claim 1 wherein the water dispersible polymer constitutes from about 0.5 weight percent to about 20 weight percent based on the weight of the composition.

21. The composition of claim 1 wherein the swellable hydrophilic carrier constitutes from about 25 weight percent to about 40 weight percent based on the weight of the composition.

22. The composition of claim 1 wherein the ratio of the amount by weight of the osmotic agent to the amount by weight of the swellable hydrophilic carrier is less than about 2.

* * * * *